United States Patent [19]

Hutson, Jr. et al.

[11] Patent Number: 4,544,777
[45] Date of Patent: Oct. 1, 1985

[54] COMBINATION ALKYLATION-ETHERIFICATION PROCESS

[75] Inventors: Tom Hutson, Jr., Galveston, Tex.; Paul D. Hann, Bartlesville, Okla.

[73] Assignee: Phillips Petroleum Company, Bartlesville, Okla.

[21] Appl. No.: 664,194

[22] Filed: Oct. 24, 1984

[51] Int. Cl.$^4$ ............................................. C07C 41/05
[52] U.S. Cl. ............................ 568/697; 585/331; 585/723; 44/53; 203/21; 203/23; 203/25
[58] Field of Search ......................................... 568/697

[56] References Cited

U.S. PATENT DOCUMENTS

| | | | |
|---|---|---|---|
| 3,069,483 | 12/1962 | Bauer | 260/683.48 |
| 3,763,022 | 10/1973 | Chapman | 203/25 |
| 3,846,088 | 11/1974 | Brown et al. | 44/56 |
| 3,979,461 | 9/1976 | Ancillotti et al. | 260/614 A |
| 4,180,526 | 12/1979 | Chapman | 585/719 |
| 4,182,924 | 1/1980 | Chapman | 585/712 |
| 4,189,616 | 2/1980 | Liebert | 585/701 |
| 4,192,825 | 3/1980 | Chapman | 585/719 |
| 4,225,741 | 9/1980 | Chapman | 585/719 |
| 4,270,929 | 6/1981 | Dang Vu et al. | 44/56 |

Primary Examiner—Howard T. Mars
Attorney, Agent, or Firm—Howard D. Doescher

[57] ABSTRACT

In a combination alkylation-methyltertiary butyl ether (MTBE) operation, isobutane vapor side-draw and bottoms product yield from the alkylation fractionation, respectively, are used to indirectly heat the mid-section and reboil section of the methyltertiary butyl ether fractionator for heat conservation, beneficiating both the alkylation operation and the MTBE operation.

6 Claims, 1 Drawing Figure

COMBINATION ALKYLATION-ETHERIFICATION PROCESS

BACKGROUND OF THE INVENTION

This invention relates to an alkylation process and the recovery of the produced hydrocarbon phase in a more efficient manner and to the preparation of tert-alkyl ethers. in accordance with another aspect, this invention relates to the exchange of heat in a combination alkylation-etherification process. In one of its aspects, it relates to a process for conserving the heat produced in an alkylation process and utilizing same in the recovery of tert-alkyl ethers in the effluent of the etherification process. In accordance with another aspect, it relates to a process for supplying heat to a fractionation zone in a combination alkylation-etherification process.

Alkylation of isoparaffinic hydrocarbons with olefinic hydrocarbons is well known as a commercially important process for producing gasoline boiling range hydrocarbons. Also, it is known that tert-alkyl ethers can be prepared by reacting a primary alcohol with an olefin having a double bond on a tertiary carbon atom, such as the reaction of methanol with isobutylene and isoamylenes to form methyl tert-butyl ether, when using isobutylene. The energy requirements and costs for the recovery of tert-alkyl ethers can be great, and it is, therefore, necessary to maintain the energy requirements for an etherification process at a low level. This is particularly important where energy is valuable and the products for generating energy are in relatively short supply and expensive. It has been found that by maximizing the use of available waste heat and an alkylation fractionation system and an etherification fractionation system that the energy requirements of an etherification can be reduced thereby resulting in great energy savings.

Accordingly, it is an object of this invention to provide an improved etherification process wherein the outside energy requirements are reduced.

Another object of this invention is to utilize excess energy available in an alkylation process as energy for an etherification process recovery system.

Still another object of this invention is to provide an efficient alkylation-etherification process which maximizes the possible use of available waste heat in the system.

Other aspects, objects and advantages of the present invention will become apparent from a study of the disclosure, the appended claims and the drawing.

SUMMARY OF THE INVENTION

In accordance with the invention, a combination alkylation-etherification process that is energy efficient is provided which comprises utilizing at least two high energy containing streams recovered from the alkylation process fractionation recovery system as the source of heat energy for the operation of the primary fractionation zone following etherification.

In a specific embodiment of the invention in a combination alkylation-etherification operation isobutane vapor side-draw and bottoms alkylate product yield from the alkylation fractionation, respectively, are used to indirectly heat an intermediate portion and the reboil or bottoms portions of the etherification fractionation for heat conservation.

Thus, the invention relates to the utilization of at least two high energy containing streams obtained from an alkylation unit product fractionation system in order to supply the energy needed in the principal tert-alkyl ether fractionation unit which has a high heat duty requirement.

In a specific embodiment of the invention in a combination alkylation-etherification process and product recovery systems improvement comprises reboiling the tert-alkyl ether fractionation unit with hot alkylation kettle product removed from the alkylation unit product fractionation and a stream of vaporous, primarily isobutane, containing side-draw removed from the alkylation product fractionation which is condensed to provide heat through an intermediate heat exchange zone positioned in the tert-alkyl ether fractionation unit. Thus, according to the present invention the main fractionation of the alkylation unit supplies two heat sources at different temperatures for the tert-alkyl fractionation unit.

BRIEF DESCRIPTION OF THE DRAWING

The drawing illustrates a combination etherification and alkylation process.

DETAILED DESCRIPTION OF THE INVENTION

Figure 1:
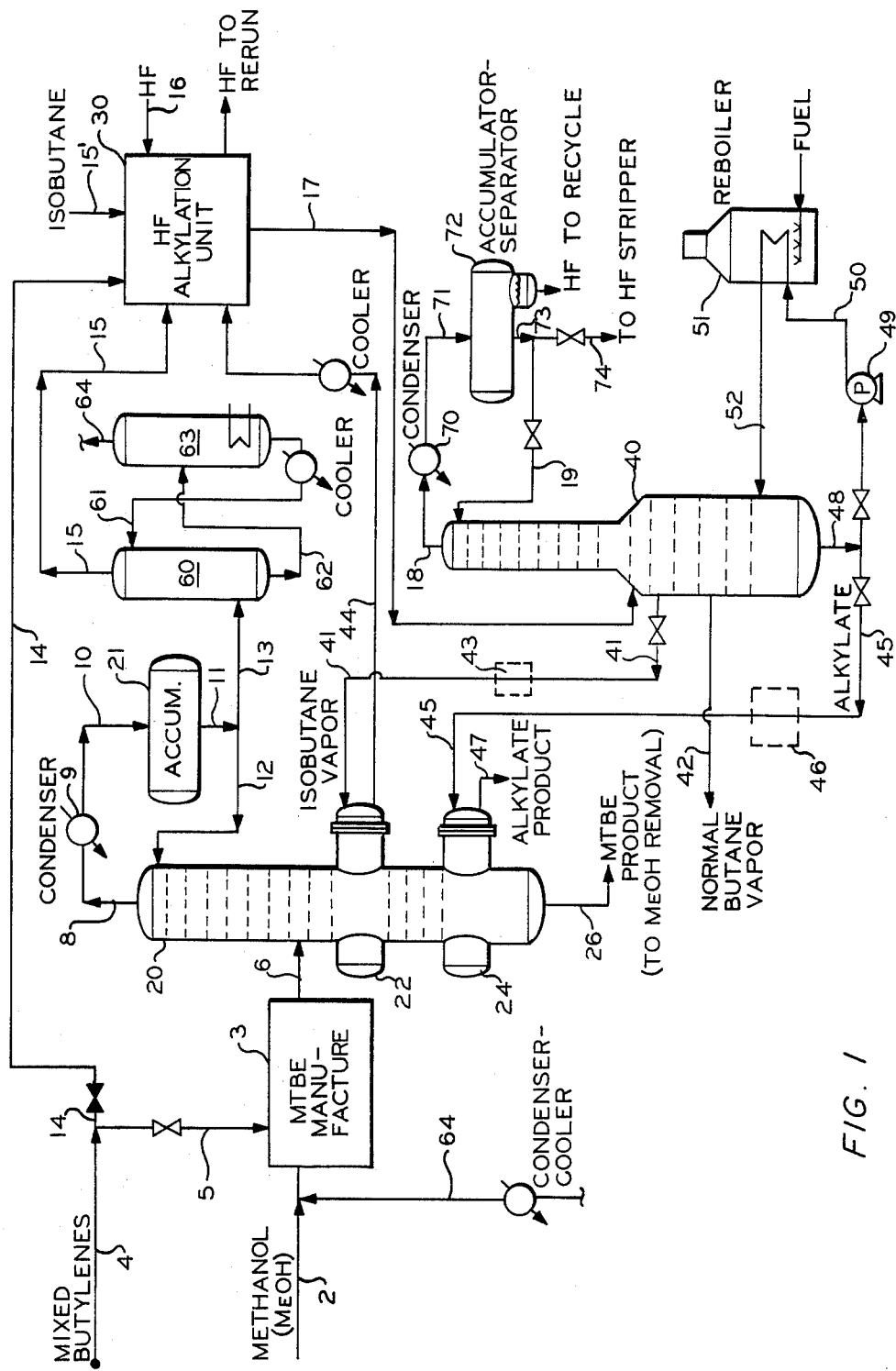

The instant invention is primarily directed to an improved fractionation system following an alkylation process in which energy is used efficiently and effectively in a fractionation system following the etherification process thereby reducing energy costs for the recovery of tert-alkyl ether and the recovery of alkylate following alkylation.

A better understanding of the invention will be obtained by reference to the accompanying drawing which shows an arrangement of an apparatus representing a preferred embodiment of the invention.

The drawing depicts schematically the relationship of the invention taking two streams of differing temperatures from an alkylation product fractionation unit and applying that heat to a fractionation unit recovering tert-alkyl ether, specifically methyl tertiary butyl ether (MTBE), at two different temperatures and physical location levels and two indirect heat exchangers in the MTBE fractionation unit.

Various stream flow arrangements are illustrated on the drawing to show the flexibility of the operation for producing gasoline and gasoline blending components in an energy efficient manner.

Referring now to the drawing, a mixed butylenes-containing stream 4 is passed by way of line 5 and introduced into etherification unit 3 wherein it is mixed with methanol or other conventionally used alcohols introduced by way of line 2. Conditions within unit 3 are such that the reactants methanol and isobutylene are converted to methyl tertiary-butyl ether which is removed along with unreacted butylenes from unit 3 by way of line 6 and introduced into an intermediate portion of fractionation zone 20.

The reaction between the butylenes cut and methanol is conventionally performed in the presence of an acid catalyst. The usual operating conditions are a temperature from about 0° to about 65° C., more often from about 10° to about 40° C. Etherification reaction is well known.

Fractionation unit 20 is operated under conditions such that an overhead stream 8 comprises unreacted butenes and some methanol, and a bottom stream 26 comprising MTBE product and methanol.

Fractionation 20 is operated generally at a kettle temperature of about 250° to about 280° F. and a pressure of about 100 to about 140 psia. The top temperature in column 20 will range from about 120° to about 170° F. and a pressure of about 90 to about 130 psia.

Fractionation zone 20 is provided with heat exchange zone 22 positioned at an intermediate portion of the fractionator and a reboiler exchange unit 24 located near the bottom of fractionator 20. Intermediate heater 22 is ordinarily operated at a temperature of about 220° F. and 100 psia and is used to condense isobutane vapor recovered from a fractionation unit to be described herein below.

Fractionator 20 kettle product comprises MTBE contaminated with methanol and is passed by way of conduit 26 to conventional methanol removal (not shown).

Overhead stream 8 comprising straight chain butenes contaminated with methanol is passed through condenser 9 and passed by way of conduit 10 to overhead accumulator 21 wherein the condensate is collected. Condensate is removed by line 11 from accumulator 21 and a portion is passed as reflux by way of line 12 and introduced in an upper portion of fractionator 20.

The remainder or yield portion of the butenes-methanol condensate removed from accumulator 21 is passed by way of line 13 to a water wash column 60 wherein it is contacted countercurrently with water introduced by way of line 61, recovered from stripper 63. Unit 60 is operated under conditions such that methanol is substantially removed from the butenes stream by the water which is removed from a lower portion of column 60 by way of line 62 and passed to stripper 63 wherein methanol and water are separated. The water is recycled by way of a cooler (not numbered) and line 61 to column 60, and the methanol is condensed and cooled and passed by way of line 64 to MTBE unit 3, or for other use as desired.

The water washed butenes steam 15 removed from unit 60 is passed after drying (not shown) to alkylation 30 wherein it is contacted with isobutane introduced by way of line 15' and alkylation catalyst, e.g. HF acid, by way of line 16.

The alkylation reaction is conducted under conventional conditions for aliphatic alkylation. The alkylation is suitably carried out by the reaction of the mixture of hydrocarbons comprising isoparaffins containing from 4 to 8 carbon atoms and olefins containing 3 to 8 carbon atoms. The isoparaffins most commonly used as feedstock for motor gasoline alkylate are isobutane and isopentane. The olefins most commonly used are propylene and butenes. Preferred feedstocks currently are isobutane and a butylenes mixture. In this specific example, isobutane is reacted with the mainly straight chain butylenes remaining from the MTBE plant.

The hydrocarbon phase comprising alkylate, isobutane, normal butane and $C_3$ and lighter hydrocarbons is removed from unit 30 by way of line 17 and passed to fractionation column 40.

Column 40 is operated under conditions such that propane and lighter hydrocarbon vapors are taken overhead by way of line 18, a vaporous sidestream 41 comprising isobutane, a vaporous hydrocarbon stream 42 comprising normal butane, and a bottoms liquid stream comprising alkylate by way of line 48. Conventionally, column 40 is operated in this example at an upper temperature of about 156° F. and 225 psia and a bottoms temperature of about 420° F. and a pressure of about 230 psia. The temperature of the column near the isobutane withdrawal is normally about 250° F.

The overhead stream 18 is passed through condenser 70 line 71 and introduced into overhead accumulator 72. The hydrocarbon condensate is removed by line 73 and a portion is passed as reflux 19 to an upper portion of column 40. The remainder or yield is removed as product for further use as desired by way of line 74. In this example, this stream comprises propane with some HF and is charged to an HF stripper (not shown) to yield stripper bottoms product of LPG quality propane.

A bottom stream comprising alkylate is removed from tower 40 by way of line 48 and thereafter is split into two streams, one passing by way of pump 49 line 50, heater 51, and line 52 for return to a lower portion of fractionation unit 40 to provide reboiler heat.

The other bottom stream comprising alkylate removed from tower 40 is passed by way of line 45 to reboiler 24 positioned in the lower portion of fractionation unit 20 whereupon this alkylate product is cooled in the reboiler and exits reboiler 24 by way of conduit means 47. The alkylate stream 45 cycled through reboiler 24 provides one source of heat for column 20.

Vaporous isobutane removed from column 40 by way of line 41 is passed through inner heater 22 positioned at an intermediate point in column 20 wherein the isobutane vapor is condensed and removed from heater 22 by way of line 44 and reintroduced after additional cooling, not numbered, into alkylation 30.

Heat exchangers 43 and 46 are used only in the event etherification 10 is shut down so as to cool the vaporous isobutane stream and alkylate stream, respectively. Similarly, if MTBE unit 10 is shut down, the olefinic butenes can be passed directly by way of conduit 14 to HF alkylation unit 30. It is also within the scope of the invention to pass mixed butenes to both units 3 and 30 when both are in operation.

As can be seen from the above description of the drawing the invention comprises reboiling the MTBE-butylene fractionator 20 with the hot alkylation kettle product 45 removed from the alkylation unit product fractionator 40, and a stream of vaporous, primarily isobutane, containing side-draw 41 removed from the alkylation product fractionator 40 is condensed to provide through a second inner heater or reboiler 22 in the MTBE-butylene fractionator. Thus, maximum heat removal is made of hot alkylation kettle product with remaining heat duty requirements of the MTBE butene fractionator 20 being provided by the condensing side-draw of essentially isobutane vapor from the alkylate product fractionator 40. Thus, in accordance with the invention, a main fractionator of the alkylation unit supplies two heat sources with different temperatures for another fractionation unit, specifically the MTBE fractionator 20.

EXAMPLE I

A calculated example as herewith given in order to illustrate one set of possible operating conditions in accordance with the invention.

| Calculated Operation | |
|---|---|
| 1. Operating conditions (Specific Operation) | Range |
| (20) MTBE-n Butenes Fractionator | |

| -continued Calculated Operation | |
|---|---|
| 1. Operating conditions (Specific Operation) | Range |
| (8) Top Zone | |
| Pressure psia | 90–130 |
| Temperature °F. | 120–170 |
| (22) Interheater Zone | |
| Pressure psia | 100–140 |
| Temperature °F. | 200–220 |
| (24) Kettle Reboiler Zone | |
| Pressure psia | 100–140 |
| Temperature °F. | 250–280 |
| (21) Accumulator | |
| Pressure psia | 70–100 |
| Temperature °F. | 100–140 |
| (40) Alkylation Product Fractionator | |
| (18) Top Zone | |
| Pressure psia | 225–245 |
| Temperature °F. | 156–164 |
| (41) Isobutane Side draw | |
| Pressure psia | 227–247 |
| Temperature °F. | 203–250 |
| (42) Normal Butane Side Draw | |
| Pressure psia | 228–248 |
| Temperature °F. | 243–290 |
| (48) Kettle Bottom Zone | |
| Pressure psia | 230–250 |
| Temperature °F. | 423–448 |

Estimated heat duty available from heat in the alkylate product (45) is 6 to 15 million Btu/HR, while MTBE kettle reboiler (24) duty is 8–12 million Btu/HR. Isobutane side draw (41) is 2–5 million Btu/HR available to heat interheater (22).

Various valves, pumps, coolers, etc., are not shown on FIG. 1 in order to simplify the drawing.

This invention has intercooperation between and mutual beneficiation of two dissimilar units. The MTBE unit prepares the normal butylenes-rich stream (having reacted out isobutene therefrom to make MTBE by reaction with methanol) for the HF alkylation of isobutane and, at the same time, receives the needed heating of the MTBE fractionation at two different temperature levels from two separate streams issuing from the HF alkylation fractionator, while, at the same time, cooling these two streams from the alkylation, this cooling of one stream (recycle isobutane) prepares this stream so that it can be processed at its proper temperature for recycle to the alkylation.

That which is claimed is:

1. A combination energy efficient process for producing high quality and gasoline blending components which comprises the steps of
   (a) contacting a mixture of methanol and an olefinic $C_4$ cut comprising isobutene, isobutane and at least one normal butene under isobutene etherification conditions to produce methyl tertiarybutyl ether (MTBE) and unreacted $C_4$ olefinic hydrocarbons,
   (b) passing the reaction effluent from step (a) to a fractionation zone operated under conditions to recover an overhead stream comprising normal butenes and some methanol, and a bottom stream comprising MTBE and methanol,
   (c) contacting at least a portion of said overhead stream in step (b) with isoparaffin and an acid alkylation catalyst under alkylation conditions in a alkylation zone to produce a hydrocarbon fraction comprising alkylate, normal butane, isobutane, and propane and lighter materials,
   (d) passing the hydrocarbon reaction effluent from alkylation in step (c) to a fractionation zone operated under conditions sufficient to recover an overhead stream comprising propane and lighter hydrocarbons, a first intermediate vaporous stream comprising isobutane, a second intermediate vaporous stream comprising normal butane, and a bottom stream comprising substantially liquid alkylate product,
   (e) passing said bottom stream in step (d) directly without substantial cooling to indirect heat exchange through boiling zone in a lower portion of said fractionation zone in step (b) as a source of reboiler heat for said fractionation zone, and
   (f) passing said intermediate vaporous stream comprising isobutane in step (d) through an intermediate heat exchange zone positioned in said fractionation zone in step (b) to condense said isobutane and release heat as an additional source of heat for said fractionation zone.

2. A process according to claim 1 wherein said isobutane stream in step (f) is returned to said alkylation zone in step (c) after being cooled and condensed in said intermediate heat exchange zone.

3. A process according to claim 1 wherein at least a portion of said olefinic $C_4$ cut passed as feed to the etherification and reaction in step (a) is passed as at least a portion of the feed to alkylation in step (c).

4. A process according to claim 1 wherein the overhead stream from each fractionation is cooled, condensed, and at least a portion of condensate from each is returned as reflux to each fractionation zone.

5. A process according to claim 1 wherein the MTBE methanol bottom stream in step (b) is passed to a water wash zone to remove methanol therefrom which methanol, after water removal, is returned to an etherification in step (a) and a purified MTBE product substantially free of methanol is recovered as a product of the process as a gasoline blending component.

6. A process according to claim 1 wherein said alkylate bottom stream and said isobutane intermediate vaporous stream provide the sole source of heat for said MTBE fractionation zone in step (a).

* * * * *